(12) United States Patent
Zlotnick et al.

(10) Patent No.: US 12,138,366 B2
(45) Date of Patent: Nov. 12, 2024

(54) MAGNETO-PATTERNED-CELL-LADEN HYDROGEL MATERIALS AND METHODS OF MAKING AND USING SAME

(71) Applicants: United States Government as represented by the Department of Veterans Affairs, Washington, DC (US); The Trustees of the University of Pennsylvania, Philadelphia, PA (US)

(72) Inventors: Hannah M. Zlotnick, Philadelphia, PA (US); Andrew Todd Clark, North Wales, PA (US); Robert L. Mauck, Philadelphia, PA (US); Xuemei Cheng, Bryn Mawr, PA (US)

(73) Assignees: The United States Government as Represented by the Department of Veterans Affairs, Washington, DC (US); The Trustees of the University of Pennsylvania, Philadelphia, PA (US)

( * ) Notice: Subject to any disclaimer, the term of this patent is extended or adjusted under 35 U.S.C. 154(b) by 208 days.

(21) Appl. No.: 17/229,829

(22) Filed: Apr. 13, 2021

(65) Prior Publication Data
US 2021/0316044 A1    Oct. 14, 2021

Related U.S. Application Data

(60) Provisional application No. 63/009,419, filed on Apr. 13, 2020.

(51) Int. Cl.
*A61L 27/38*    (2006.01)
*A61L 27/04*    (2006.01)
(Continued)

(52) U.S. Cl.
CPC ......... *A61L 27/3847* (2013.01); *A61L 27/042* (2013.01); *A61L 27/045* (2013.01);
(Continued)

(58) Field of Classification Search
CPC .. A61L 27/3847; A61L 27/042; A61L 27/045; A61L 27/047; A61L 27/222;
(Continued)

(56) References Cited

U.S. PATENT DOCUMENTS 8,815,231 B2    8/2014    Souza et al.
2005/0266394 A1    12/2005    Hatton et al.
(Continued)

FOREIGN PATENT DOCUMENTS

WO    WO2013019212    2/2013
WO    WO2017062600    4/2017

OTHER PUBLICATIONS

Fu, Chien-Yu, et al. "A simple cell patterning method using magnetic particle-containing photosensitive poly (ethylene glycol) hydrogel blocks: a technical note." Tissue Engineering Part C: Methods 17.8 (2011): 871-877. (Year: 2011).*
(Continued)

*Primary Examiner* — Benjamin J Packard
*Assistant Examiner* — Joshua A Atkinson
(74) *Attorney, Agent, or Firm* — Ballard Spahr LLP

(57) ABSTRACT

The present disclosure is concerned with magneto-patterned cell-laden hydrogel materials and methods of making and using those materials. The disclosed materials are useful for, among other things, repair of tissue defects, e.g., tissue at a tissue interface such as a bone-cartilage interface.

20 Claims, 14 Drawing Sheets

(51) Int. Cl.
*A61L 27/22* (2006.01)
*A61L 27/46* (2006.01)
*A61L 27/52* (2006.01)

(52) U.S. Cl.
CPC ............ *A61L 27/047* (2013.01); *A61L 27/222* (2013.01); *A61L 27/225* (2013.01); *A61L 27/3852* (2013.01); *A61L 27/46* (2013.01); *A61L 27/52* (2013.01); *A61L 2300/258* (2013.01); *A61L 2300/402* (2013.01); *A61L 2300/406* (2013.01); *A61L 2300/408* (2013.01); *A61L 2300/41* (2013.01); *A61L 2300/414* (2013.01); *A61L 2300/426* (2013.01); *A61L 2300/43* (2013.01)

(58) Field of Classification Search
CPC .... A61L 27/225; A61L 27/3852; A61L 27/46; A61L 27/52; A61L 2300/258; A61L 2300/402; A61L 2300/406; A61L 2300/408; A61L 2300/41; A61L 2300/414; A61L 2300/426; A61L 2300/43
See application file for complete search history.

(56) References Cited

U.S. PATENT DOCUMENTS

| | | |
|---|---|---|
| 2010/0273230 A1 | 10/2010 | Bhakdi et al. |
| 2011/0076665 A1 | 3/2011 | Gatenholm et al. |
| 2018/0133372 A1 | 5/2018 | Rinaldi et al. |
| 2019/0046692 A1 | 2/2019 | Shefi et al. |

OTHER PUBLICATIONS

Kim, Jungju, et al. "Bone regeneration using hyaluronic acid-based hydrogel with bone morphogenic protein-2 and human mesenchymal stem cells." Biomaterials 28.10 (2007): 1830-1837. (Year: 2007).*
Bermejo-Velasco, Daniel, et al. "Injectable hyaluronic acid hydrogels with the capacity for magnetic resonance imaging." Carbohydrate polymers 197 (2018): 641-648. (Year: 2018).*
Zlotnick et al., "Magneto-patterned mesenchymal stem cell laden hydrogels recapitulate cartilaginous matrix gradients," Abstract for presentation at Orthopaedic Research Society meeting on Feb. 8-11, 2020.
Zlotnick et al., "Magneto-patterned mesenchymal stem cell laden hydrogels recapitulate cartilaginous matrix gradients," Presentation at Orthopaedic Research Society meeting on Feb. 8-11, 2020.
Zlotnick et al., "Magneto-patterned mesenchymal stem cell laden hydrogels recapitulate cartilaginous matrix gradients," Poster presented at Orthopaedic Research Society meeting on Feb. 8-11, 2020.
Anil-Inevi, et al. (2018) "Biofabrication of in situ Self Assembled 3D Cell Cultures in a Weightlessness Environment Generated using Magnetic Levitation," *Sci Rep.*, 8(1), 10 pages.
Burdick, et al. (2005) "Controlled Degradation and Mechanical Behavior of Photopolymerized Hyaluronic Acid Networks," *Biomacromolecules*, 6(1) pp. 386-391.
Durmus, et al. (2015) "Magnetic Levitation of Single Cells," *Proc Natl Acad Sci*, 112 (28) pp. 3661-3668.
Grogan, et al. (2012) "In Situ Tissue Engineering Using Magnetically Guided Three-Dimensional Cell Patterning," 2012; *Tissue Eng*, Part B, 18 (7) pp. 496-506.
Huang, et al. (2014) "Light Addressable Electrodeposition of Magnetically-Guided Cells Encapsulated in Alginate Hydrogels for Three-Dimensional Cell Patterning,"*Micromachines*, 5, pp. 1173-1187.
Jin, et at. (2008) "Differences in magnetically induced motion of diamagnetic, paramagnetic and superparamagnetic microparticles detected by cell tracking velocimetry." *The Analyst*. 133(12):1767-1775.
Kim, et al. (2017) "Enhanced Nutrient Transport Improves the Depth-Dependent Properties of Tri-Layered Engineered Cartilage Constructs with Zonal Co-Culture of Chondrocytes and MSCs," *Acta Biomater*, 58, pp. 1-11.
Klein, et al. (2007) "Depth-Dependent Biomechanical and Biochemical Properties of Fetal, Newborn, and Tissue-Engineered Articular Cartilage," *J. Biomech*., 40(1) 182-190.
Kostura, et al. (2004) "Feridex Labeling of Mesenchymal Stem Cells Inhibits Chondrogenesis But Not Adipogenesis or Osteogenesis," *NMR Biomed*, 17(7) pp. 513-517.
Krebs, et al. (2009) "Formation of ordered cellular structures in suspension via label-free negative magnetophoresis," *Nano Lett.*, 9(5) pp. 1812-1817.
Li, et al. (2018) "Glycosylated superparamagnetic nanoparticle gradients for osteochondral tissue engineering." *Biomaterials*. 176, pp. 24-33.
Nam, et al. (2013) "Magnetic Separation of Malaria-Infected Red Blood Cells in Various Development Stages," *Anal. Chem.*, 86(15) pp. 7316-7323.
Ng, et al (2009) "Zonal Chondrocytes Seeded in a Layered Agarose Hydrogel Create Engineered Cartilage with Depth-Dependent Cellular and Mechanical Inhomogeneity," *Tissue Eng*, Part B, 15 pp. 2315-2324.
Shen, et al. (2012) "Label-Free Cell Separation Using a Tunable Magnetophoretic Repulsion Force," *Analyt Chem*, 84:pp. 3075-3081.
Tasoglu, et al. (2014) "Guided and Magnetic Self-Assembly of Tunable Magnetoceptive Gels," *Nature Communications*, DOI: 10.1038/ncomms5702 11 pages.
Tocchio, et al. (2018) "Magnetically Guided Self-Assembly and Coding of 3D Living Architectures." *Advanced Materials*. 30(4), pp. 1-15.
Winkleman, et al. (2004) "A Magnetic Trap for Living Cells Suspended in a paramagnetic Buffer" App. Phys. Let. 85(12) p. 2411, https://doi.org/10.1063/1.1794372.
Yaman, et al. (2018) "Magnetic Force-Based Microfluidic Techniques for Cellular and Tissue Bioengineering," *Frontiers in Bioengineering and Biotechnology*, 6 (192) 29 pages.
Zhao, et al. (2016) "Label-Free Microfluidic Manipulation of Particles and Cells in Magnetic Liquids," *Adv. Funct. Mater.*, 26 (22) pp. 3916-3932.
Zhu et al. (2018) Mimicking Cartilage Tissue Zonal Organization by Engineering tissue-Scale Gradient Hydrogels as 3D Cell Niche, Tissue Eng Part A, 24:1-10, 2018.

* cited by examiner

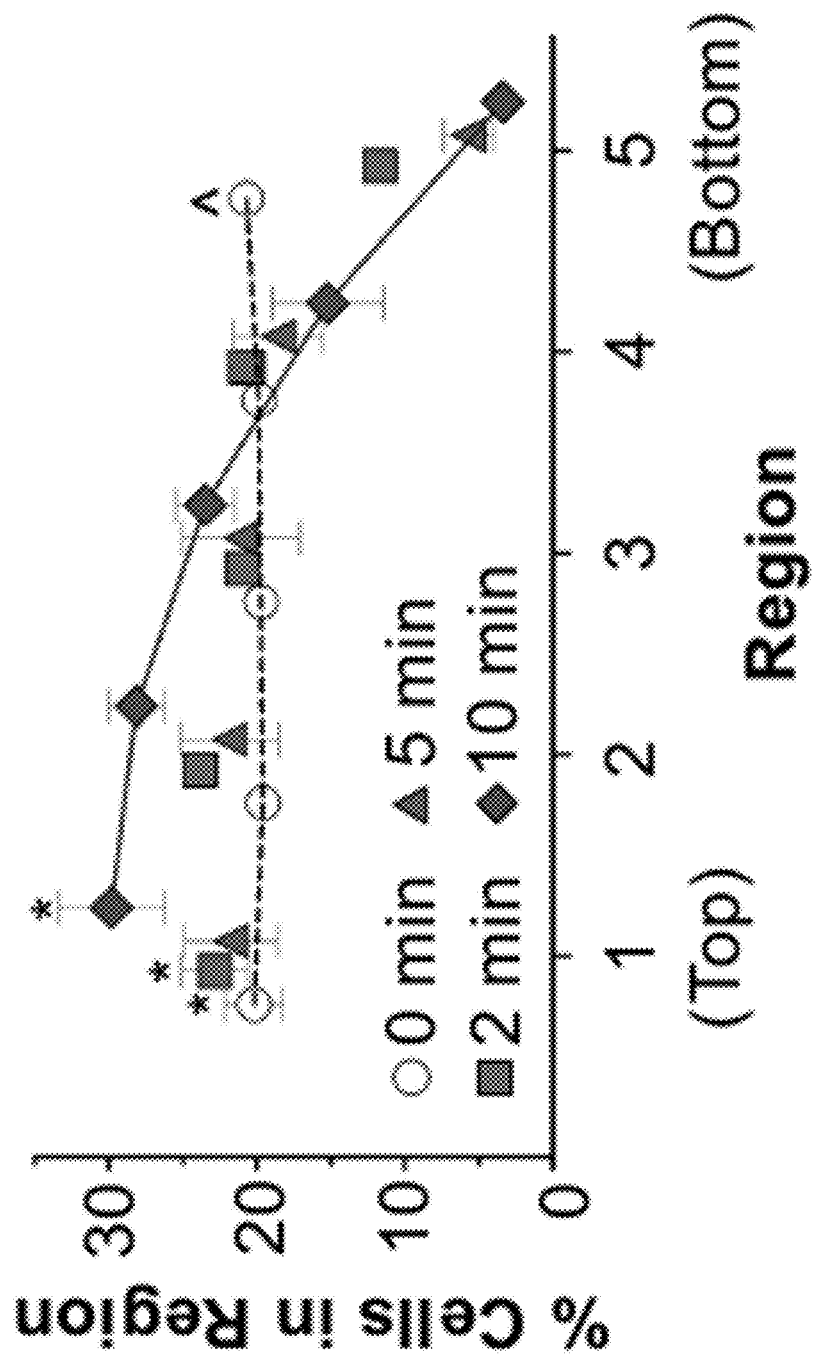

MAGNETO-PATTERNED-CELL-LADEN HYDROGEL MATERIALS AND METHODS OF MAKING AND USING SAME

CROSS-REFERENCE TO RELATED APPLICATIONS

This application claims the benefit of U.S. Provisional Application No. 63/009,419, filed Apr. 13, 2020, which is incorporated by reference in its entirety.

STATEMENT REGARDING FEDERALLY SPONSORED RESEARCH

This invention was made with government support under grant number IK6 RX003416 awarded by the Department of Veterans' Affairs, grant number CMMI: 15-48571 awarded by the National Science Foundation, and grant numbers R01EB008722, T32-AR007132, and P30AR069619 awarded by the National Institutes of Health and the National Institute of Arthritis and Musculoskeletal and Skin Diseases. The government has certain rights in the invention.

BACKGROUND

Engineering tissue for the repair or regeneration of an interface that includes two different tissue types presents a challenge. Tissue interfaces are often defined by cell and signaling gradients, in which the cellularity of a particular type of tissue is present in a zonal structure or pattern. In general, current tissue engineering methods for repair of tissue at an interface have shown limited success due to their failure to mimic the zonal organization of native tissue.

For instance, repairing tissue at a chondral defect is difficult. A chondral defect is a focal area of damage to the articular cartilage (the cartilage that lines the end of bone). Osteochondral defects refer to a focal area of damage that involves both the cartilage and a piece of underlying bone. The cellularity of articular cartilage decreases from the superficial zone to the deep zone of the tissue. The superficial tissue zone is comprised primarily of soft cartilage, whereas the deep zone is close to the bony end of tissue and is mechanically stiff. Cell shape, orientation, and biologic activity also vary through tissue zones. Tissue engineering methods for osteochondral repair in particular have been hampered by their failure to mimic native tissue zones.

Thus, there remains a need for improved methods and materials for repairing certain tissue defects. These needs and others are met by the present disclosure.

SUMMARY

In accordance with the purpose(s) of embodied and broadly described herein, this disclosure, in one aspect, relates to magneto-patterned cell-laden hydrogel materials and methods of making and using those materials.

The disclosed materials and methods are useful for, among other things, repair of tissue, e.g., tissue at an interface that includes two different types of tissue, such as the bone-cartilage interface. Specifically, a magnetic field can be used to pattern cells within a hydrogel material that can then be cross-linked to lock the cells in place, thereby providing a tissue construct that mimics the zonal nature of the underlying defective tissue and improves integration of engineered tissues.

Thus, in various aspects, disclosed are continuous hydrogel materials comprising a paramagnetic or superparamagnetic salt and cells, the cells being arranged in a gradient within the continuous hydrogel material.

Also disclosed are continuous hydrogel materials comprising non-magnetically-labeled cells arranged in a gradient within the continuous hydrogel material.

Also disclosed are methods of producing a continuous hydrogel material comprising the following steps: (a) providing a viscous mixture comprising a hydrogel precursor, a paramagnetic or superparamagnetic salt, crosslinking agent, and cells in a mold; (b) creating a gradient of the cells in the viscous mixture by exposing the viscous mixture to a magnetic field; and (c) crosslinking the hydrogel precursor, thereby producing the continuous hydrogel material having a gradient of the cells.

Also disclosed are hydrogel materials made from any of the disclosed methods.

Also disclosed are methods for improving the repair, formation, or regeneration of tissue (e.g., cartilage and/or bone) at a defective site within a subject, comprising implanting a disclosed hydrogel material into a subject at the defective site.

BRIEF DESCRIPTION OF THE FIGURES

The accompanying figures, which are incorporated in and constitute a part of this specification, illustrate several aspects and together with the description serve to explain the principles of the invention.

FIG. 6A and FIG. 6B show an image (6A) of cell distribution in hydrogels after magnetic field exposure and a plot (6B) showing % cells in a region of a construct over time.

Figure 1:
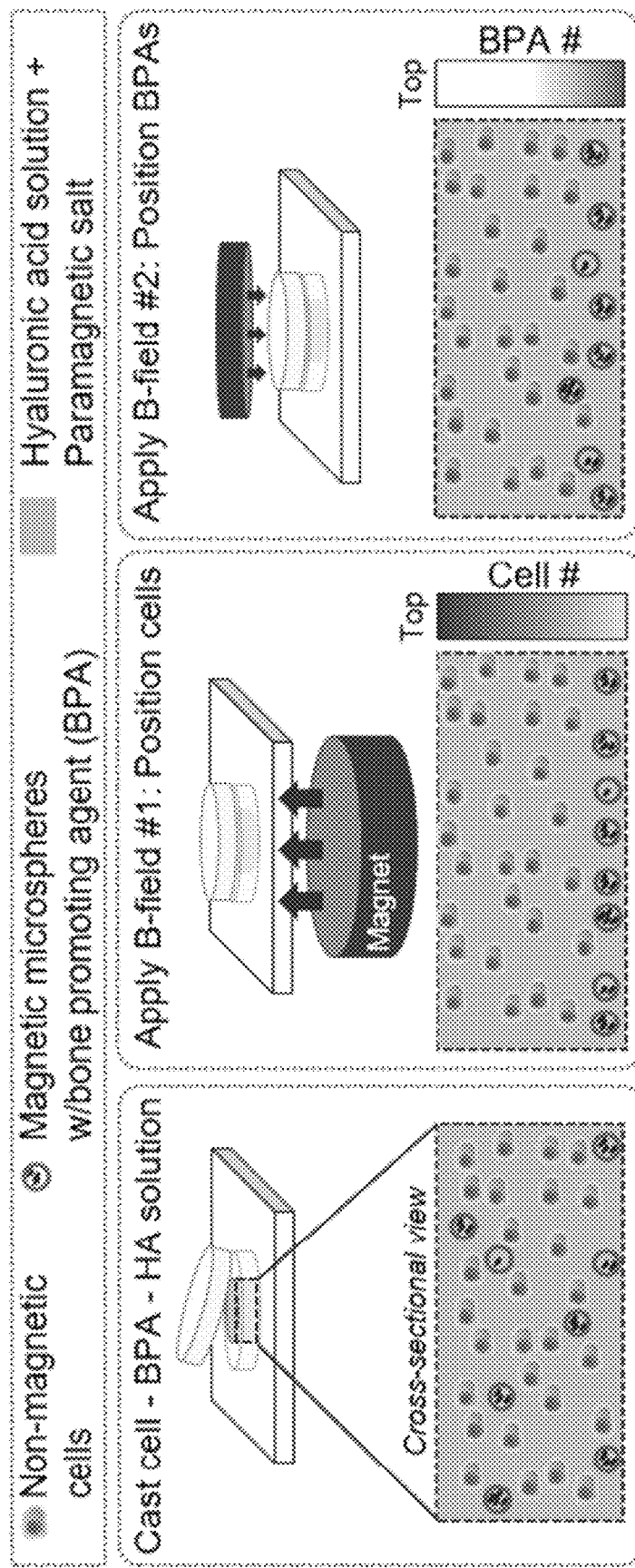
FIG. 1 shows an exemplary scheme depicting the magneto-patterning of a disclosed continuous hydrogel material.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present invention can be understood more readily by reference to the following detailed description and examples.

Before the present materials and methods are disclosed and described, it is to be understood that the materials are not limited to specific methods of making unless otherwise specified. It is also to be understood that the terminology used is for the purpose of describing particular aspects only and is not intended to be limiting. Although any methods and materials similar or equivalent to those described can be used in the practice or testing of the present materials and methods, example materials and methods are now described.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a hydrogel material" includes mixtures of two or more such hydrogel materials.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians" Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the materials of the disclosure as well as the materials themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular material is disclosed and discussed and a number of modifications that can be made to a number of molecules including the compounds are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination material, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this disclosure including, but not limited to, steps in methods of making and using the materials. Thus, if there are a variety of additional steps that can be performed it is understood that each of these additional steps can be performed with any specific embodiment or combination of embodiments of the methods of the invention.

It is understood that the disclosed materials have certain functions. Disclosed are certain structural requirements for performing the disclosed functions, and it is understood that there are a variety of structures that can perform the same function that are related to the disclosed materials, and that these materials will typically achieve the same result.

B. CONTINUOUS HYDROGEL MATERIALS

In various aspects, the continuous hydrogel material comprises a paramagnetic or superparamagnetic salt and cells, the cells being arranged in a gradient within the continuous hydrogel material. The paramagnetic or superparamagnetic salt increases the magnetic susceptibility of the hydrogel precursor comprising the cells and, in some aspects, other objects such as magnetic objects (e.g., an object in a superparamagnetic, paramagnetic, ferromagnetic, or ferrimagnetic state) and an active agent, thereby allowing a magnetic field to pattern the cells and other optional objects within the hydrogel precursor. The hydrogel precursor can then be crosslinked such that the cells and other optional objects are locked into place.

In further aspects, the continuous hydrogel material comprises cells arranged in a gradient within the continuous hydrogel material. Thus, in some aspects, the continuous hydrogel material is substantially free of the one or more paramagnetic or superparamagnetic salts used to increase the magnetic susceptibility of the hydrogel precursor used to make the continuous hydrogel material. In a further aspect, the hydrogel material is substantially free or free of paramagnetic or superparamagnetic salts.

1. Paramagnetic or Superparamagnetic Salts

Any suitable paramagnetic or superparamagnetic salt can be used to increase the magnetic susceptibility of the hydrogel precursor. In general, a paramagnetic or superparamagnetic salt contains one or more transition metal ions that have at least one unpaired electron in their electron configuration. In one aspect, the salt is paramagnetic and comprises a salt of gadolinium, manganese, iron, chromium, cobalt, nickel, or neodymium. Non-limiting examples include salts of gadolinium(III), e.g., gadolinium dichloride, gadodiamide (a gadolinium-based MRI contrast agent), manganese(II) salts, e.g., manganese chloride, iron(III) salts, e.g., iron chloride, chromium(III) salts, e.g., chromium chloride, cobalt(III) salts, e.g., cobalt chloride, nickel(II) salts, e.g., nickel chloride, and neodymium(III) salts, e.g., neodymium chloride. In a further aspect, the paramagnetic salt is gadodiamide (also known as gadolinium diethylene triamine penta-acetic acid bis-methylamide, or GD-DTPA-BMA). In a still further aspect, the paramagnetic salt is gadobutrol (Gd-BT-DO3A), gadopentetate dimeglumine (Gd-DPTA), gadoterate meglumine (Gd-DOTA), gadobenate dimeglumine (Gd-BOPTA), or a combination thereof 2. Cells The cells in the hydrogel material can be any type of cell. The disclosed hydrogel materials and methods are not limited to any particular type of cell. In one aspect, the cells in the continuous hydrogel materials can be any cells useful for tissue engineering, e.g., the engineering of tissues at the interface of more than one tissue type, such as tissue at the cartilage-bone interface.

In one aspect, the cells are naturally diamagnetic such that the cells need not be magnetically-labeled to magnetopattern within the hydrogel precursor. Thus, in some aspects, the cells in the hydrogel material are label-free, e.g., not labeled with any magnetic label. In a further aspect, the cells in the hydrogel material do not have any magnetic particles tethered to or within the cells. In a still further aspect, the cells in the hydrogel material do not have any particles comprising iron (e.g., iron oxide particles) tethered to or within the cells.

In various aspects, the cells in the hydrogel material are selected from stem cells (e.g., mesenchymal stromal/stem cells), chondrocytes, chondroprogenitors, tenocytes, tendon progenitor cells, osteoblasts, osteocytes, osteoclasts, fibroblasts, induced pluripotent stem cells, embryonic stem cells, adipose derived stem cells, infrapatellar fat-pad derived stem cells, meniscal fibrochondrocytes, or a combination thereof.

In one aspect, the cells in the hydrogel material are stem cells. The term "stem cell," as used herein, refers to undifferentiated cells having high proliferative potential with the ability to self-renew that can generate daughter cells that can undergo terminal differentiation into more than one distinct cell phenotype. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

In various aspects, the stem cells in the hydrogel material are selected from mesenchymal stromal/stem cells, induced pluripotent stem cells, embryonic stem cells, adipose derived stem cells, infrapatellar fat-pad derived stem cells, or a combination thereof.

In a further aspect, the cells in the hydrogel material are mesenchymal stem cells (MSCs), also known as bone marrow stromal stem cells or skeletal stem cells. MSCs are non-blood adult stem cells found in a variety of tissues. They are characterized by their spindle-shape morphologically, by the expression of specific markers on their cell surface, and by their ability, under appropriate conditions, to differentiate along a minimum of three lineages (osteogenic, chondrogenic, and adipogenic).

The arrangement of cells in the continuous hydrogel material can vary depending on the application. In one aspect, the gradient of cells in the continuous hydrogel material is substantially linear throughout the continuous hydrogel material. In a further aspect, the gradient of cells in the continuous hydrogel material is arranged along a longitudinal axis of the continuous hydrogel material. In a still further aspect, the gradient of cells in the continuous hyrogel material is arranged along a transverse axis to a longitudinal axis of the continuous hydrogel material. In another aspect, the gradient of cells in the continuous hydrogel material is such that a portion of the continuous hydrogel material has at least twice the concentration of cells as compared to another portion of the continuous hydrogel material. In a further aspect, the gradient of the cells is such that a portion of the continuous hydrogel material has at least five times the concentration of cells as compared to another portion of the continuous hydrogel material.

In a further aspect, the percentage of cells in the continuous hydrogel material increases along an axis of the continuous hydrogel material. Thus, in some aspects, an axis of the continuous hydrogel material can extend through several arbitrary regions of the hydrogel material, each region having a different percentage of cells. For example, in a continuous hydrogel material comprising five arbitrary regions of equal area, the percentage of cells in each region can vary as described in the Table below. Thus, the percentage of cells at any given point along an axis of the continuous hydrogel material can depend on which region the point along the axis is located.

EXEMPLARY CELL GRADIENT TABLE

| Aspect | Region 1 | Region 2 | Region 3 | Region 4 | Region 5 |
|--------|----------|----------|----------|----------|----------|
| 1 | 20-25% | 20-25% | 15-20% | 15-20% | 10-15% |
| 2 | 20-25% | 20-25% | 15-20% | 15-20% | 5-10% |
| 3 | 30-35% | 20-25% | 20-25% | 15-20% | 0-5% |

In some aspects, the continuous hydrogel material, as discussed in more detail below, is formed from poly(ethylene oxide), poly(vinyl alcohol), poly(acrylic acid), poly(propylene fumarate-co-ethylene glycol), poly(ethylene glycol), a polypeptide, agarose, alginate, chitosan, collagen, fibrin, gelatin, hyaluronic acid, or a combination thereof. In one aspect, the continuous hydrogel material is formed from hyaluronic acid. In a further aspect, the continuous hydrogel material is formed by crosslinking hyaluronic acid.

In one aspect, the continuous hydrogel material comprises mesenchymal stem cells arranged in a gradient within the hydrogel material formed from hyaluronic acid. In a further aspect, the continuous hydrogel material comprises mesenchymal stem cells arranged in a gradient within the hydrogel material that comprises hyaluronic acid and a paramagnetic or superparamagnetic salt comprising a gadolinium salt, e.g., gadodiamide (gadolinium diethylene triamine penta-acetic acid bis-methylamide, GD-DTPA-BMA). In another aspect, the paramagnetic or superparamagnetic salt has been washed out of the continuous hydrogel material once the hydrogel precursor has been crosslinked and the cells are locked into place. Thus, in some aspects, the continuous hydrogel material is substantially-free of the paramagnetic or superparamagnetic salt used to increase the magnetic susceptibility of the hydrogel precursor.

3. Magnetic Objects

In some aspects, the continuous hydrogel material further comprises magnetic objects comprising a magnetic material and an active agent, the magnetic objects being arranged in a gradient within the continuous hydrogel material that is opposite the gradient of the cells within the continuous hydrogel material. In a further aspect, the continuous hydrogel material further comprises magnetic objects comprising a magnetic material and an active agent, the magnetic objects being arranged in a gradient within the continuous hydrogel material that is opposite the gradient of the diamagnetic cells within the continuous hydrogel material. Thus, according to this aspect, the population of magnetic objects can be positioned opposite the diamagnetic cells. In one aspect, the continuous hydrogel material comprises magnetic objects comprising a magnetic material that is in a superparamagnetic, paramagnetic, ferromagnetic, or ferrimagnetic state. Examples of magnetic materials include without limitation materials comprising one or more of iron, manganese, copper, cobalt, or nickel. In a further aspect, the magnetic material comprises iron, e.g., iron oxide.

In one aspect, the magnetic object (e.g., an object in a superparamagnetic, paramagnetic, ferromagnetic, or ferrimagnetic state) is a drug delivery microcapsule. Thus, in various aspects, the drug delivery microcapsule comprises an active agent encapsulated within the microcapsule.

In one aspect, the active agent in the magnetic object (e.g., an object in a superparamagnetic, paramagnetic, ferromagnetic, or ferrimagnetic state) is an agent useful for generating or regenerating tissue. In a further aspect, the active agent in the magnetic object (e.g., an object in a superparamagnetic, paramagnetic, ferromagnetic, or ferrimagnetic state) is an agent useful for generating or regenerating tissue at a tissue interface, e.g., the bone-cartilage interface.

For example, one aspect, the active agent is a bone-promoting agent. As used herein, a "bone-promoting agent" is a substance that promotes and/or induces bone formation. In various aspects, the bone-promoting agent present in the magnetic object can be any bone-promoting agent known in the art. Non-limiting examples of bone promoting agents include growth factors such as bone morphogenetic protein ("BMP") (Sulzer Orthopedics), BMP-2 (Genetics Institute/Sofamor Danek), basic fibroblast growth factor (bFGF) (Orquest/Anika Therapeutics), Epogen (Amgen), granulocyte colony-stimulating factor (G-CSF) (Amgen), Interleukin growth factor (IGF)-1 (Celtrix Pharmaceuticals), osteogenic protein (OP)-1 (Creative BioMolecules/Stryker Biotec), platelet-derived growth factor (PDGF) (Chiron), stem cell proliferation factor (SCPF) (University of Florida/Advanced Tissue Sciences), recombinant human interleukin (rhIL) (Genetics Institute), transforming growth factor beta (TGRβ) (Collagen Corporation/Zimmer Integra Life Sciences), and TGFβ-3 (OSI Pharmaceuticals).

In a further aspect, the bone-promoting agent comprises a calcium source, a phosphate source, bone morphogenetic factor, an anti-resorptive agent, an osteogenic factor, a cartilage-derived morphogenetic protein, a growth hormone, an estrogen, a biphosphonate, a statin, a differentiation factor, or a combination thereof.

In some aspects, the active agent in the magnetic object (e.g., an object in a superparamagnetic, paramagnetic, ferromagnetic, or ferrimagnetic state) is a therapeutic agent. A variety of therapeutic agents can be used depending on the desired application. In one aspect, the active agent in the magnetic object (e.g., an object in a superparamagnetic, paramagnetic, ferromagnetic, or ferrimagnetic state) is a therapeutic agent selected from an analgesic agent, an anesthetic agent, an antimicrobial agent, an antibacterial agent, an antiviral agent, an antifungal agent, an antibiotic, an anti-inflammatory agent, an antioxidant, an antiseptic agent, an immunostimulating agents, and combinations thereof.

In some aspects, when the active agent in the magnetic object (e.g., an object in a superparamagnetic, paramagnetic, ferromagnetic, or ferrimagnetic state) is an analgesic agent, any analgesic agent known in the art can be used. For example, the analgesic agent can include, without limitation, non-steroidal anti-inflammatory drugs (NSAIDs) such as indomethacin, aspirin, diclofenac sodium, ketoprofen, ibuprofen, mefenamic acid, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone or etodolac; and steroidal drugs such as dexamethasone, dexamethasone sodium sulfate, hydrocortisone, prednisolone. The analgesic agent can also be a high-potency analgesic such as codeine, dihydrocodeine, hydrocodone, morphine, dilandid, demoral, fentanyl, pentazocine, oxycodone, pentazocine or propoxyphene.

In some aspects, when the active agent in the magnetic object (e.g., an object in a superparamagnetic, paramagnetic, ferromagnetic, or ferrimagnetic state) is an anesthetic agent, any anesthetic agent known in the art can be used. Non-limiting examples include amylocaine, articaine, benzocaine, bupivacaine, butacaine, 2-chloroprocaine, cinchocaine, dexivacaine, diamocaine, dibucaine, etidocaine, ketocaine, lidocaine, mepivacaine, oxybuprocaine, parethoxycaine, prilocaine, procaine, propanocaine, proparacaine, propoxycaine, pyrrocaine, risocaine, rodocaine, ropivacaine, tetracaine, and combinations thereof.

In some aspects, when the active agent in the magnetic object (e.g., an object in a superparamagnetic, paramagnetic, ferromagnetic, or ferrimagnetic state) an antimicrobial agent, any antimicrobial agent known in the art can be used. Non-limiting examples include natural antimicrobial agents, including macrolides, aminoglycosides, cephems, penicillins, chitosans, chitins, hyaluronic acids, alginic acids, carrageenans, xanthans, gellans, amino acids, and proteins; synthetic antimicrobial agents, including quinolones, sulfonamides, diamidines, bisphenols, guanidines, biguanides (e.g., chlorhexidine gluconate), imidazoliums, hexidines, sulfanilic acids, salicylic acids, aminobenzoic acids, hydantoins, and imidazolidinones, and mixtures thereof.

In some aspects, when the active agent in the magnetic object (e.g., an object in a superparamagnetic, paramagnetic, ferromagnetic, or ferrimagnetic state) is an antibacterial or antifungal agent, any antibacterial or antifungal agent known in the art can be used. Non-limiting examples include penicillin, ampicillin, amoxicillin, cefalexin, erythromycin ethylsuccinate, bacampicillin hydrochloride, minocycline hydrochloride, chloramphenicol, tetracycline, erythromycin, fluconazole, itraconazole, ketoconazole, miconazole, terbinafine; nlidixic acid, piromidic acid, pipemidic acid trihydrate, enoxacin, cinoxacin, ofloxacin, norfloxacin, ciprofloxacin hydrochloride, or sulfamethoxazole trimethoprim.

In some aspects, when the active agent in the magnetic object (e.g., an object in a superparamagnetic, paramagnetic, ferromagnetic, or ferrimagnetic state) is an antiviral agent, any antiviral agent known in the art can be used. Non-limiting examples include trisodium phosphonoformate, didanosine, dideoxycytidine, azido-deoxythymidine, didehydro-deoxythymidine, adefovir dipivoxil, abacavir, amprenavir, delavirdine, efavirenz, indinavir, lamivudine, nelfinavir, nevirapine, ritonavir, saquinavir or stavudine.

In some aspects, when the active agent in the magnetic object (e.g., an object in a superparamagnetic, paramagnetic, ferromagnetic, or ferrimagnetic state) is an antibiotic, any antibiotic known in the art can be used. Non-limiting examples include amoxicillin, doxycycline, cephalexin, ciprofloxacin, clindamycin, metronidazole, azithromycin, sulfur drugs, sulfamethaxazole, trimethoprim, vancomycin, teicoplanin, linezolid, daptomycin, ceftobiprole, ceftaroline, dalbacancin, fusidic acid, mupirocin, omadacycline, oritavancin, tedizolid, telavancin, tigecycline, aminoglycosides, capapenems, ceftazidime, cefepime, ceftobiprole, ceftolozane, tazobactam, fluoroquinolines, piperacillin, ticarcillin, clavulanic acid, and combinations thereof.

In some aspects, when the active agent in the magnetic object (e.g., an object in a superparamagnetic, paramagnetic, ferromagnetic, or ferrimagnetic state) is an anti-inflammatory agent, any anti-inflammatory agent known in the art can be used. In general, an anti-inflammatory agent is one that reduces inflammation and swelling. When an anti-inflammatory agent is present as the active agent in the magnetic object, the agent can be steroidal or non-steroidal. Non-limiting examples include corticosteroids, e.g., prednisone, cortisone, methylprednisolone, and combinations thereof. Other non-limiting examples include aspirin, celecoxib (Celebrex), diclofenac (Cambia, Cataflam, Voltaren-XR, Zipsor, Zorvolex), diflunisal, etodolac, ibuprofen, indomethacin, and combinations thereof.

In some aspects, when the active agent in the magnetic object (e.g., an object in a superparamagnetic, paramagnetic, ferromagnetic, or ferrimagnetic state) is an antioxidant, any antioxidant known in the art can be used. Non-limiting examples include ascorbic acid, vitamin A, vitamin E, lipoic acid, masoprocol, pramipexole, nitric oxide, allopurinol, pentoxyfylline, glutathione, uric acid, carotenes, ubiquinol (coenzyme Q), and combinations thereof.

In some aspects, when the active agent in the magnetic object (e.g., an object in a superparamagnetic, paramagnetic, ferromagnetic, or ferrimagnetic state) is an antiseptic agent, any antiseptic agent known in the art can be used. Non-limiting examples include hexachlorophene, chlorhexidine, povidone iodine, sodium hypochlorite, oxychlorosene sodium, benzalkonium chloride, silver nitrate, hydrogen peroxide, alcohols, iodine, polyhexanide (PHMB), and combinations thereof.

In some aspects, when the active agent in the magnetic object (e.g., an object in a superparamagnetic, paramagnetic, ferromagnetic, or ferrimagnetic state) is an immunostimulating agent, any immunostimulating agent known in the art can be used. Non-limiting examples include interleukins, interferons, vaccines, T-cell stimulating agents, adjuvants, e.g., Freund's complete adjuvant, PGG-glucan (BETAFECTIN) and combinations thereof.

In some aspects, the active agent in the magnetic object (e.g., an object in a superparamagnetic, paramagnetic, ferromagnetic, or ferrimagnetic state) is a more than one of an analgesic agent, an anesthetic agent, an antimicrobial agent, an antibacterial agent, an antiviral agent, an antifungal agent, an antibiotic, an anti-inflammatory agent, an antioxidant, an antiseptic agent, and an immunostimulating agent. Thus, the magnetic object (e.g., an object in a superparamagnetic, paramagnetic, ferromagnetic, or ferrimagnetic state) can, in various aspects, include more than one active agent. In one aspect, as one of skill in the art will appreciate, the amount of any particular active agent in the magnetic object (e.g., an object in a superparamagnetic, paramagnetic, ferromagnetic, or ferrimagnetic state) is an amount sufficient to achieve a desired therapeutic response.

In one aspect, the gradient of the magnetic object (e.g., an object in a superparamagnetic, paramagnetic, ferromagnetic, or ferrimagnetic state) is such that a portion of the continuous hydrogel material has at least twice the concentration of objects as compared to another portion of the continuous hydrogel material. In a further aspect, the gradient of the magnetic object (e.g., an object in a superparamagnetic, paramagnetic, ferromagnetic, or ferrimagnetic state) is such that a portion of the continuous hydrogel material has at least five times the concentration of objects as compared to another portion of the continuous hydrogel material.

C. METHODS OF MAKING THE CONTINUOUS HYDROGEL MATERIALS

In various aspects, the continuous hydrogel materials can be prepared by (a) providing a viscous mixture comprising a hydrogel precursor, a paramagnetic or superparamagnetic salt, crosslinking agent, and cells in a mold; (b) creating a gradient of the cells in the viscous mixture by exposing the viscous mixture to a magnetic field; and (c) crosslinking the hydrogel precursor, thereby producing the continuous hydrogel material having a gradient of the cells.

In a further aspect, the viscous mixture further comprises magnetic objects (e.g., an object in a superparamagnetic, paramagnetic, ferromagnetic, or ferrimagnetic state) comprising a magnetic material and an active agent, and exposing the viscous mixture to the magnetic field creates a gradient of the magnetic objects in the viscous mixture that is opposite the gradient of the cells in the viscous mixture, and crosslinking the cross-linkable hydrogel agent further produces a gradient of the magnetic objects in the continuous hydrogel material that is opposite the gradient of the cells in the continuous hydrogel material.

In some aspects, the viscous mixture has a viscosity of from about $10^{-2}$ to about 1 Pascal-second (Pass). For example, the viscous mixture can have a viscosity of about 0.01, 0.02, 0.05, 0.1, 0.2, 0.3, 0.4, 0.5, 0.6, 0.7, 0.8, 0.9, or 1 Pascal-second (Pass). Viscosity of the mixture can be measured using methods known in the art.

In one aspect, exposing the viscous mixture to the magnetic field comprises positioning a magnet close to the mold. With reference to FIG. 1, for example, a magnet can be placed close to the mold (above or below, depending on the object or cell desired for positioning). In a further aspect, the strength of the magnetic field will vary depending on the size of the mold and desired gradient positioning of cells or objects. In one aspect, for example, the viscous mixture can be exposed to a magnetic field ranging from about 1,000 Oersted (Oe) to about 5,000 Oersted (Oe), e.g., 1,000; 2,000; 3,000; 4,000; or 5,000 Oe.

Figure 2:
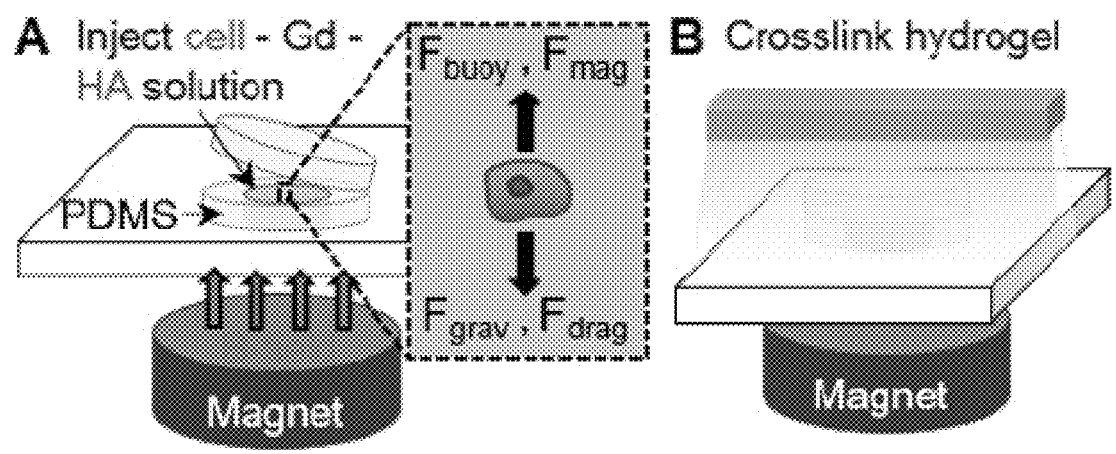
FIG. 2 shows an illustration of an exemplary magnetic setup and gel fabrication/cross-linking.

In one aspect, crosslinking the hydrogel precursor comprises exposing the hydrogel precursor to ultraviolet or visible light or heat. In a further aspect, the crosslinking step can be carried out by altering the pH of the viscous mixture. With reference to FIG. 2, for example, once the cells and other optional objects in the hydrogel precursor are positioned in a gradient or otherwise, any of the aforementioned crosslinking techniques can be used to lock the cells and other optional objects in place. In a further aspect, once the cells and other optional objects are locked into place, a further step of washing the paramagnetic or superparamagnetic salt out of the hydrogel material can be carried out.

It is understood that any of the disclosed methods of making the continuous hydrogel materials can be used with any of the hydrogel materials discussed above. Thus, in various aspects, the viscous mixture can comprise magnetic objects (e.g., an object in a superparamagnetic, paramagnetic, ferromagnetic, or ferrimagnetic state), such as a drug delivery microcapsule, including those comprising active and therapeutic agents, e.g., any of those described above. Also disclosed are continuous hydrogel materials made by any of the disclosed methods.

D. METHODS OF USING THE CONTINUOUS HYDROGEL MATERIALS

In one aspect, this disclosure relates to the use of continuous hydrogel materials. In one aspect, for example, disclosed are methods of improving the repair, formation, or regeneration of tissue (e.g., cartilage and/or bone) at a defective site within a subject, comprising implanting at the defective site any of the disclosed continuous hydrogel materials.

In a further aspect, the defective site within the subject comprises a full or partial thickness articular cartilage defect, a chondral defect, an osteochondral defect, osteoarthritis, osteochondritis dissecans, a joint defect, a defect resulting from trauma, sports, or repetitive stress, or a combination thereof.

In a further aspect, the subject has been diagnosed with a need for repair, formation, or regeneration of tissue (e.g., cartilage and/or bone) prior to the implanting step.

In a further aspect, the method of use further comprises identifying a subject in need of repair, formation, or regeneration of tissue (e.g., cartilage and/or bone).

In some aspects, the subject is a mammal. In further aspects, the subject is a human.

E. EXAMPLES

The following examples are put forth so as to provide those of ordinary skill in the art with a complete disclosure and description of how the materials and methods are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided to illustrate the disclosure but should not be construed as limiting in any way.

1. Magnetic Cell Positioning Setup

The magnetic cell positioning setup included (i) one permanent magnet ($^{15}/_{16}$-inch diameter×$^{1}/_{2}$-inch thick, Brmax=13,200 Gauss; K&J Magnetics, Inc.), (ii) a glass slide, (iii) a polydimethylsiloxane (PDMS) ring with an inner 4 mm diameter, and (iv) a PDMS cover. The PDMS ring was positioned 3.8 mm above the central axis of the magnet on the glass slide. With reference to FIG. 2, in step (A), a solution containing particles/cells, Gadodiamide (gadolinium diethylene triamine penta-acetic acid bis-methylamide, GD-DTPA-BMA), and hyaluronic acid is injected into a PDMS ring. In step (B), UV light is used to crosslink the hydrogel and stop movement of particles/cells.

2. Hydrogel Material Fabrication

A 1% w/v methacrylated hyaluronic acid (MeHA) solution (see Burdick, J A et al., Biomacromol, 6:386-91, 2005) with 0.05% photoinitiator (Irgacure) was combined with 200 mM Gadodiamide (Gd; Omniscan) and fluorescent polystyrene microspheres (10 μm diameter; 250,000 beads/mL). 20 μL of MeHA—beads—Gd solution was pipetted into the PDMS ring and covered. After either 1 minute, 3 minutes, 5 minutes, or 10 minutes of magnetic field exposure, the solution was crosslinked with UV light (λ=365 nm; intensity: 10 mW/cm2) for 10 minutes. Gels fabricated with cells used juvenile bovine mesenchymal stem cells (2 million/mL) labeled with CellTracker Far Red. Samples were cut diametrically after UV exposure and were imaged with an inverted fluorescent microscope.

3. Modeling and Simulation

The magnetic induction throughout a 2D cross section of the hydrogel (R: 0-2 mm, Z: 0-1.3 mm) was computed at each point on a 20 μm spaced rectangular grid in COMSOL. Magnetic induction values and their respective derivatives were exported into a custom MATLAB script to plot the movement of polystyrene beads (10 μm in diameter, 1.05 g/mL density) over ten minutes with a time step of 5 seconds. The molar magnetic susceptibility of gadolinium-based paramagnetic solutions is 3.2×10-4 M-1 (see Durmus, N G et al., PNAS, 112:E3661-E3668, 2015). The following equations (adapted from Durmus) were solved in MATLAB with the variables defined in Table 1.

$$F_{mag} + F_{drag} + F_{bouyant} + F_{grav} = ma$$

$$F_{mag} = \left(\frac{V\Delta\chi}{\mu_0} B \cdot \nabla\right) B$$

$$F_{drag} = 6\pi R \eta f_D v$$

$$F_{bouyant} = V\rho_f g$$

$$F_{grav} = V\rho_c g$$

TABLE 1

Variables used in model.

| Var | Description | Units | Value |
|---|---|---|---|
| V | Bead volume | μm³ | 523.6 |
| Δχ | Magnetic susceptibility of bead - Magnetic susceptibility of fluid | none | $\chi_c = 0$ $\chi_f = 6.4 \times 10^{-5}$ |
| B | Magnetic induction | T | Calculated from COMSOL |
| μ₀ | Mag permeability of free space | NA⁻² | $1.2566 \times 10^{-6}$ |
| r | Radius of bead | Mm | 2.5-20 |
| η | Dynamic viscosity of uncrosslinked hydrogel | Pa · s | $10^{-2}$-$10^{-1}$ |
| f_D | Drag coefficient | None | 1 [7] |
| v | Velocity of bead | m/s | Calculated |
| m | Mass of bead | g | $5.5 \times 10^{-7}$ |
| a | Acceleration of bead | m/s² | Calculated |
| ρ_f | Density of fluid | g/mL | 1.081 (measured) |
| ρ_c | Density of polystyrene bead | g/mL | 1.05 |
| g | Gravitational acceleration | m/s² | 9.8 |

Figure 3A:
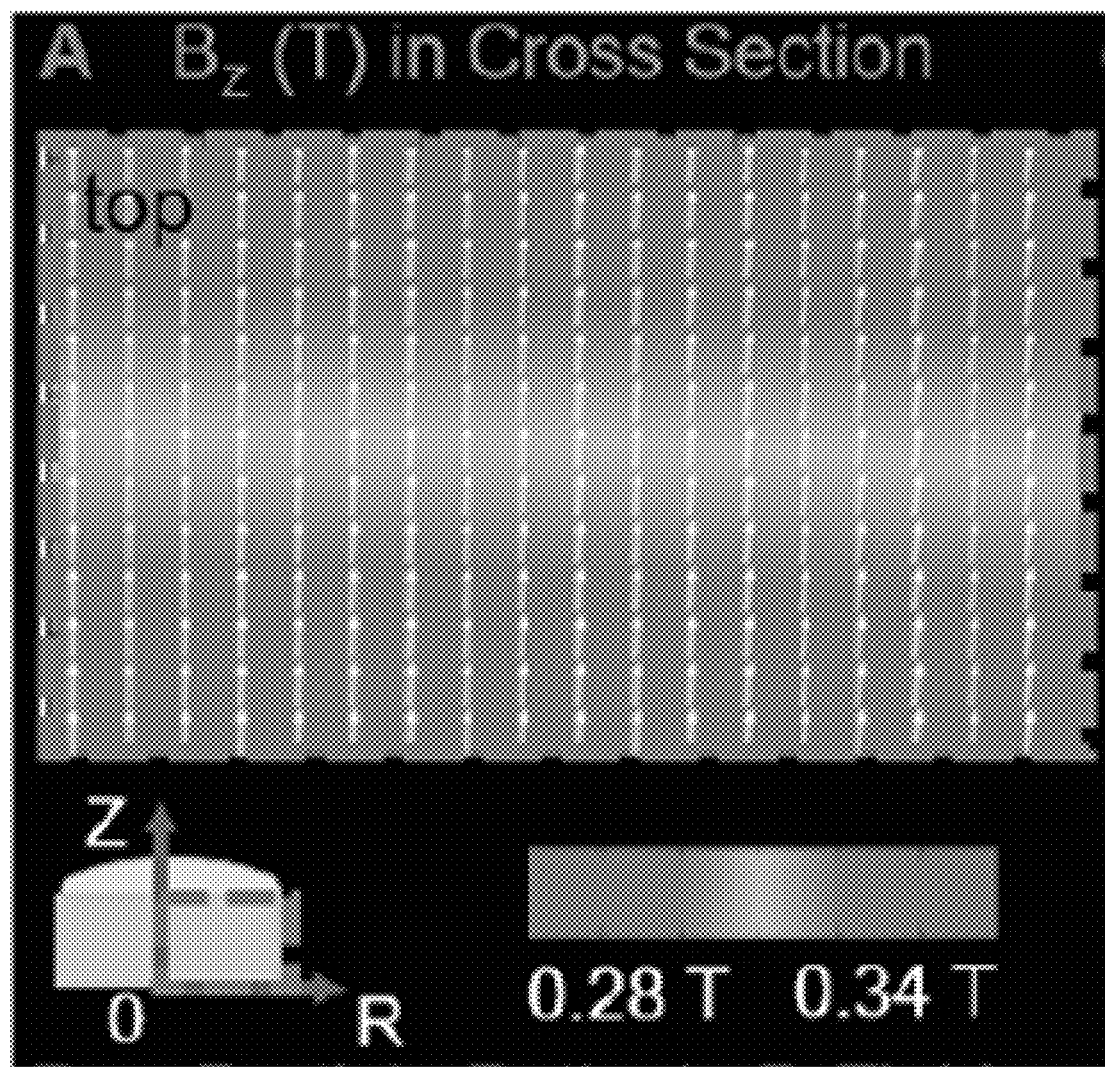
FIGS. 3A-D show results from exemplary magnetic field modeling and particle movement. (3A) COMSOL model of the magnetic induction in a 2D cross section of the hydrogel. (3B) Path of particle over 10 minutes when subjected to a magnetic field based on radius or viscosity of fluid. (3C) Simulation of polystyrene bead movement. (3D) Experimental data of polystyrene bead movement.

The stray magnetic field from an NDFeB permanent magnet was modeled in COMSOL across half of the 2D cross section of the hydrogel (FIG. 3A). The magnetic induction decreased along the Z-direction and was relatively constant along the R-direction, given that the gel was significantly smaller in diameter than the magnet. Overall, the magnetic induction ranged from 0.28 Tesla (T) to 0.34 T through the depth of the gel.

Figure 3B:
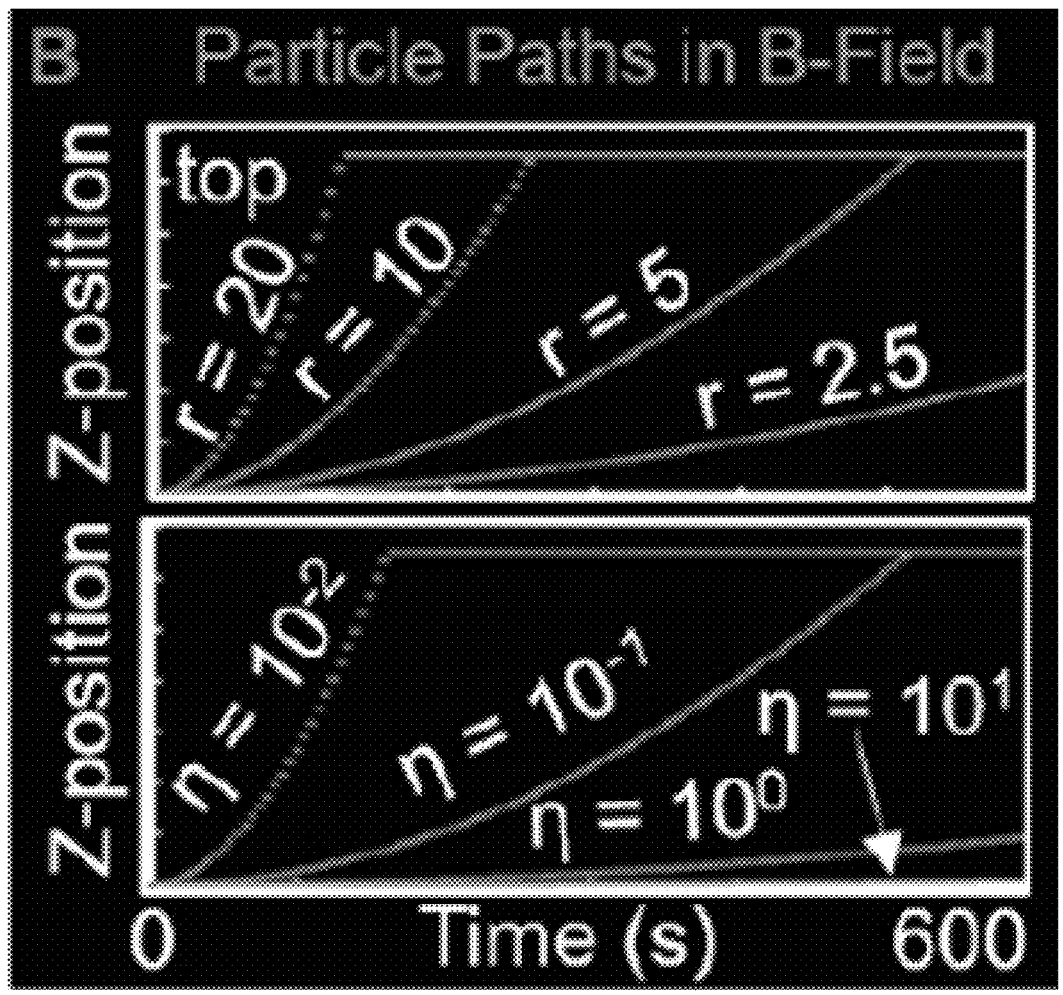
Figure 3C:
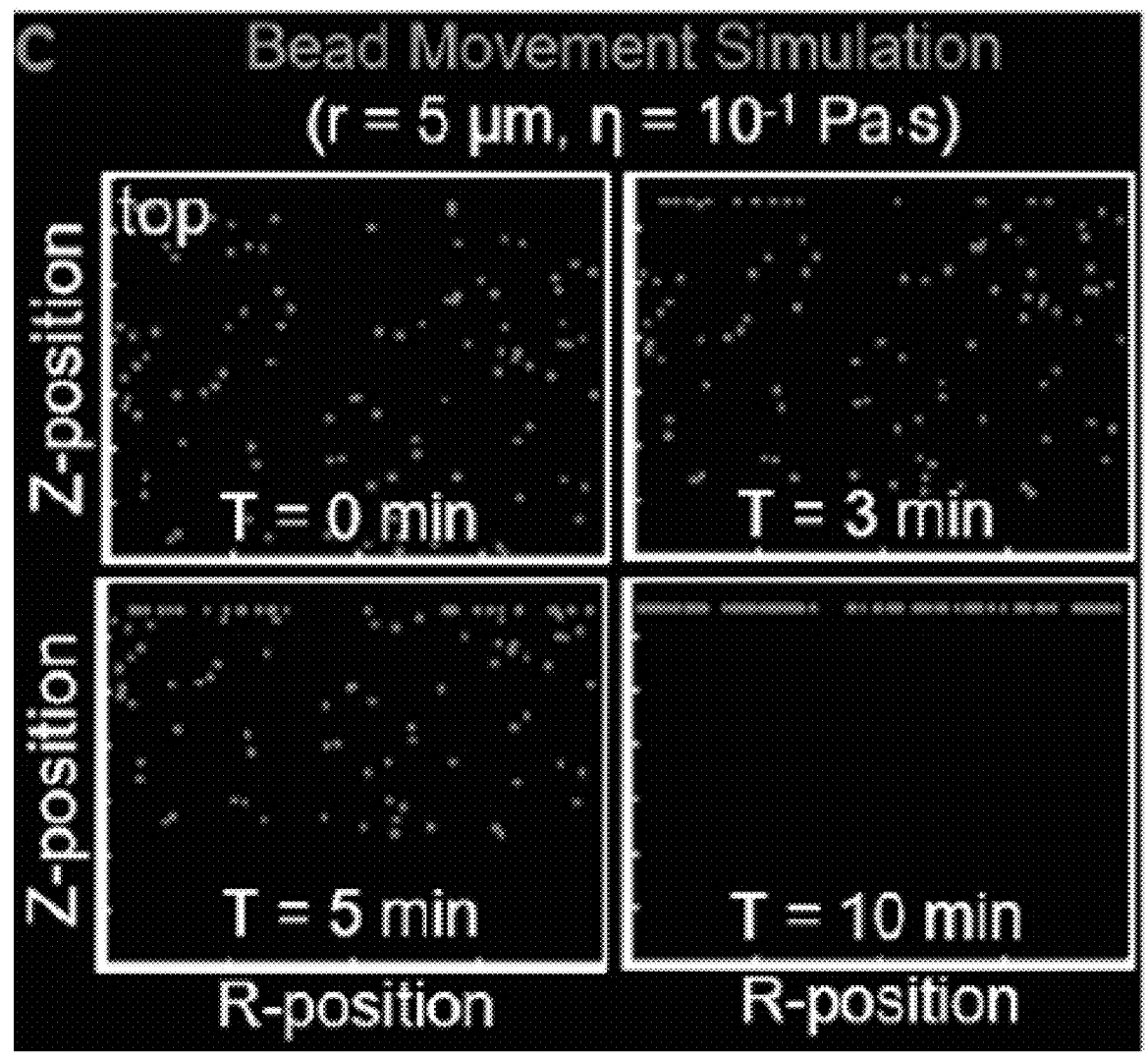
Figure 3D:
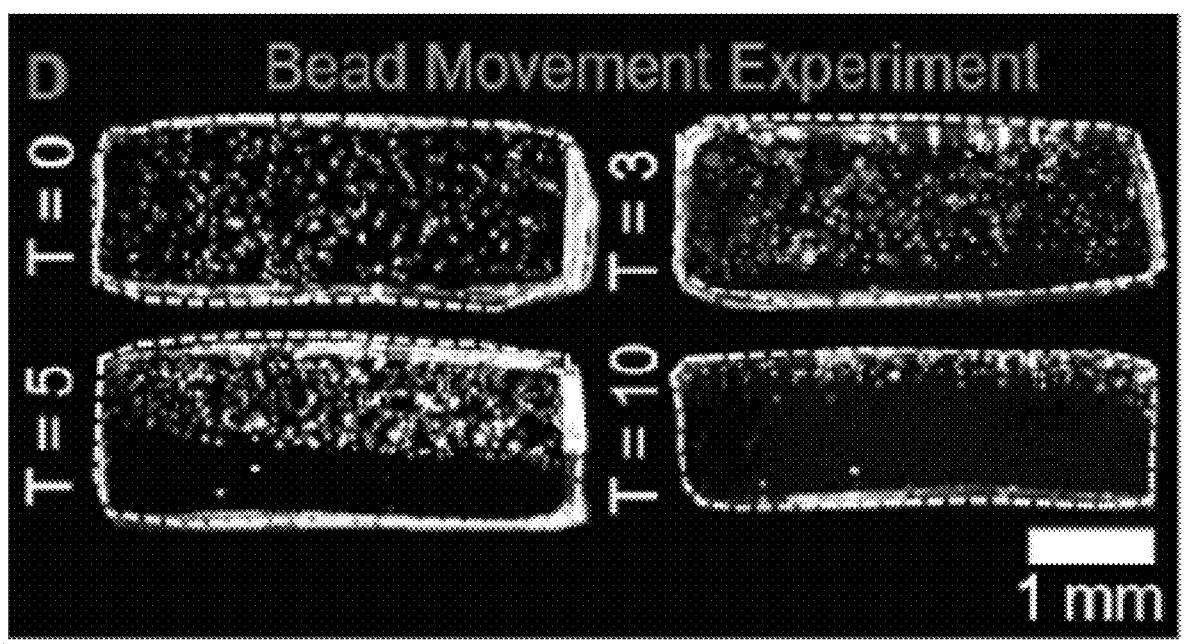

Using the MATLAB particle movement model, a parameter sweep was carried out for particle radius (r: 2.5 μm-20 μm) and fluid viscosity (η: $10_{-2}$-101 Pa·s) (FIG. 3B). Increasing radius increased drag force, while also increasing magnetic force, such that particles with a greater radius were more responsive to the applied field. Increases in viscosity slowed particle movement. To validate the model, polystyrene beads of uniform size and density were used. The model output (FIG. 3C) was strikingly similar to the experimental data acquired (FIG. 3D). Particles moved away from the magnet placed underneath the Gd-meHA solution. After 3 minutes of magnetic field exposure, there was a clear gradient of particles within the hydrogel. After 10 minutes, most beads had reached the top of the gel, similar to the model.

Figure 4:
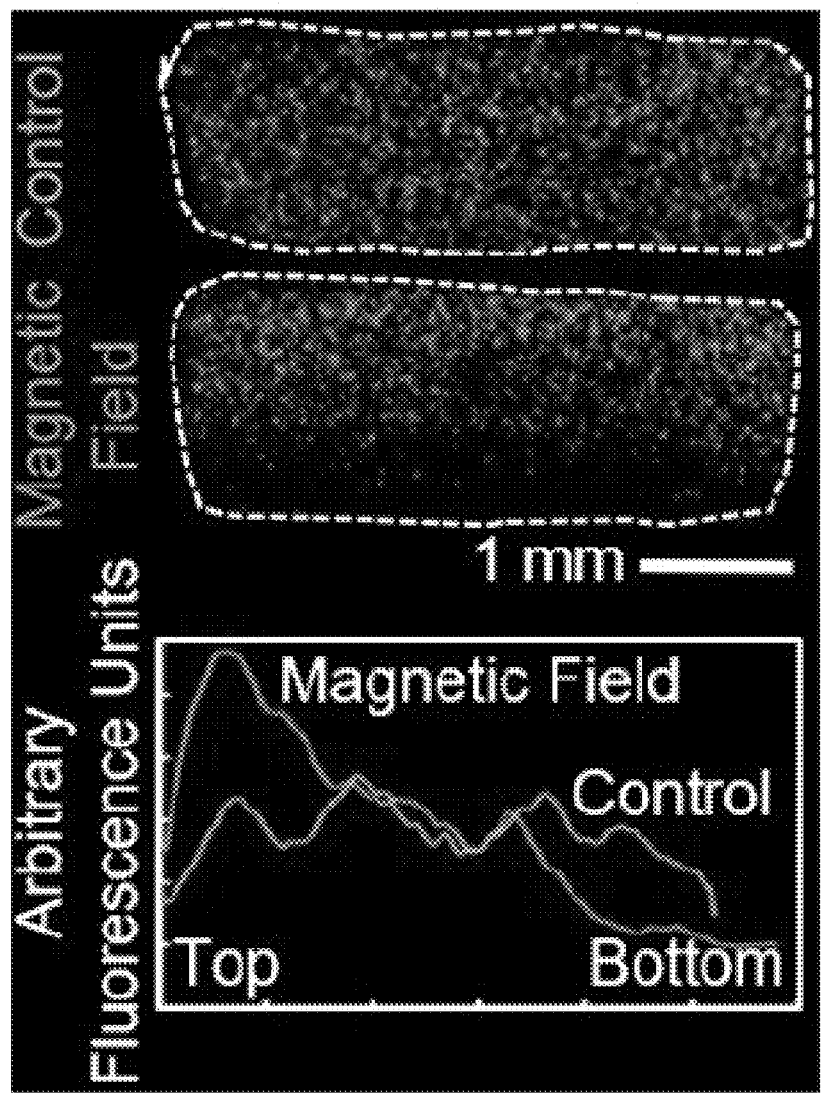
FIG. 4 shows fluorescent image results from exemplary label-free magnetic cell patterning in a hyaluronic acid gel. Fluorescent intensity was averaged across the width of a ROI from the top to the bottom of the sample cross section.

After validating the computational model, fluorescently labeled cells were mixed into the Gd-meHA solution and subjected to the same magnetic field. In control gels, the cells were evenly dispersed throughout the depth (FIG. 4). After applying the magnetic field for 5 minutes before crosslinking, there was a clear gradient from the top to the bottom of the constructs, as shown in the fluorescence intensity plot.

These data demonstrate that negative magnetophoresis may be used to pattern cells in 3D space for potential interface tissue engineering applications. A wide array of stray B-fields can be designed with additional permanent magnets. This technique is advantageous over other magnet-based methods that require iron oxide particles to be tethered to or phagocytosed by cells, since iron particles can negatively affect cell differentiation (see Kostura, L et al., NMR Biomed, 17:513-517, 2004). Additionally, the computational model may be used to expedite experimental work focused on patterning objects of known density and diameter in a paramagnetic fluid.

4. Paramagnetic Agent Diffusion

Figure 5:
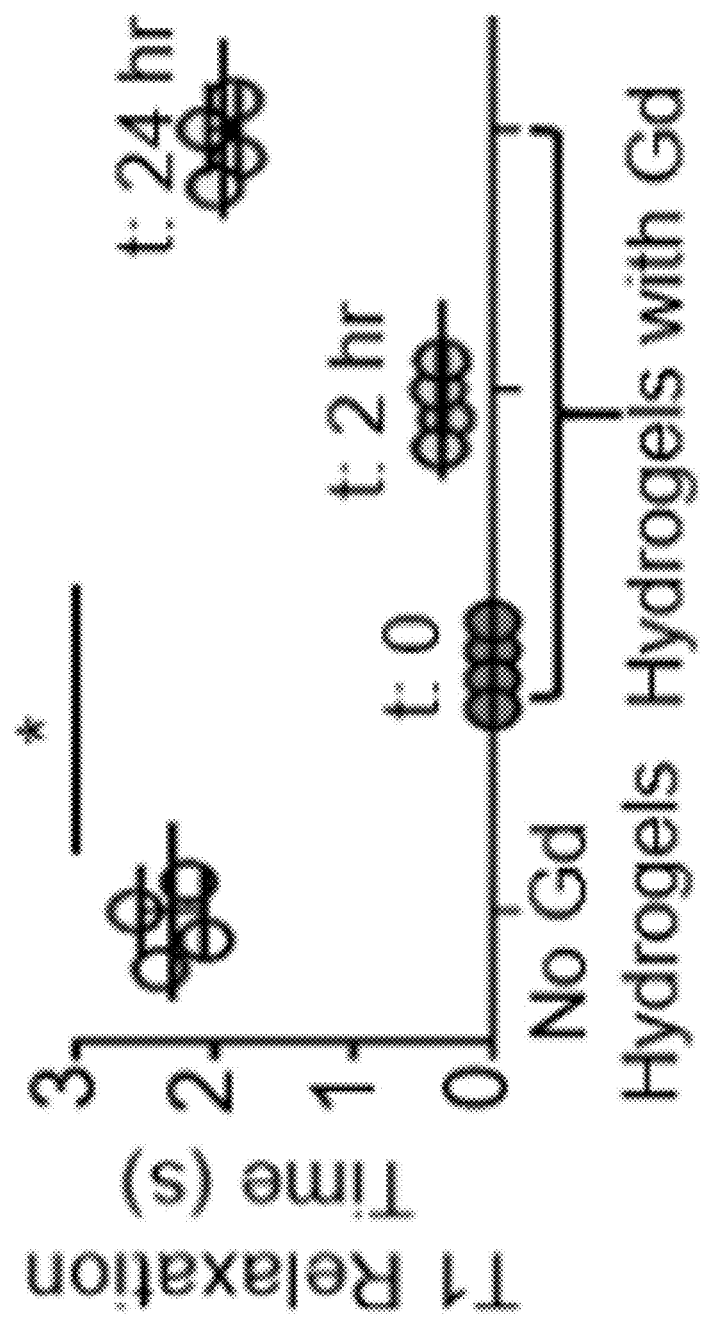
FIG. 5 shows a plot of diffusion of Gadodiamide (gadolinium diethylene triamine penta-acetic acid bis-methylamide, GD-DTPA-BMA) out of acellular crosslinked hydrogels.

With reference to FIG. 5, which shows a plot of Gadodiamide (gadolinium diethylene triamine penta-acetic acid bis-methylamide, GD-DTPA-BMA) diffusion out of acellular crosslinked hydrogels, a 4.7 T MRI acquired images of hydrogels +/−$Gd^3$. Samples were manually contoured and an IDL code calculated T1 relaxation times. Time indicates incubation duration in media.

5. Cell Positioning, Viability, and Recapitulation

Figure 6A:
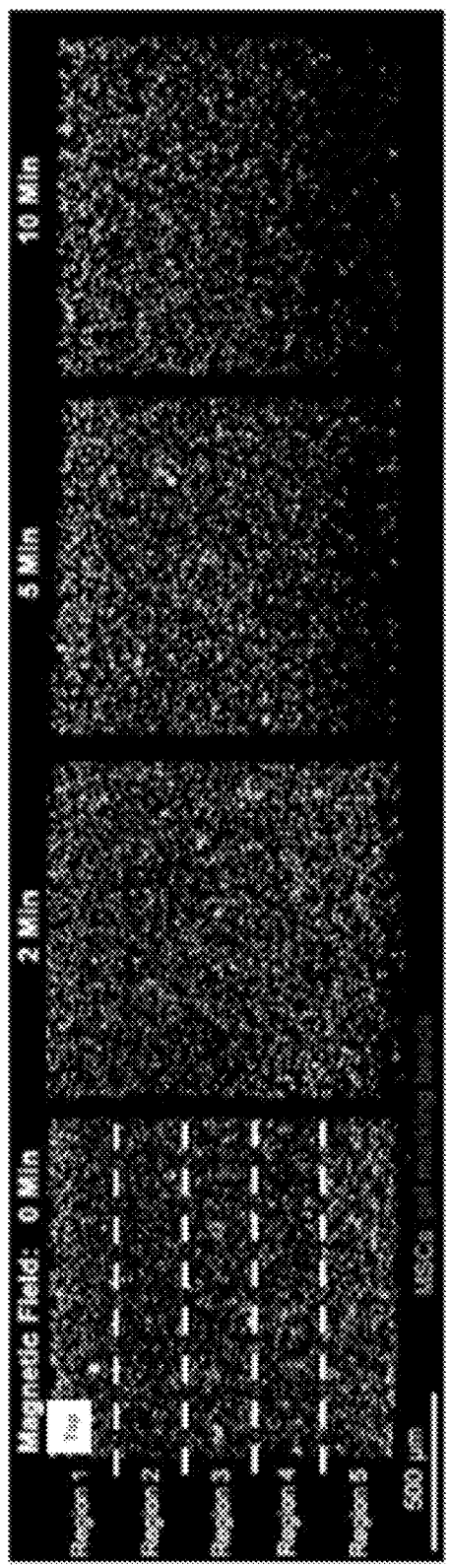
Figure 7:
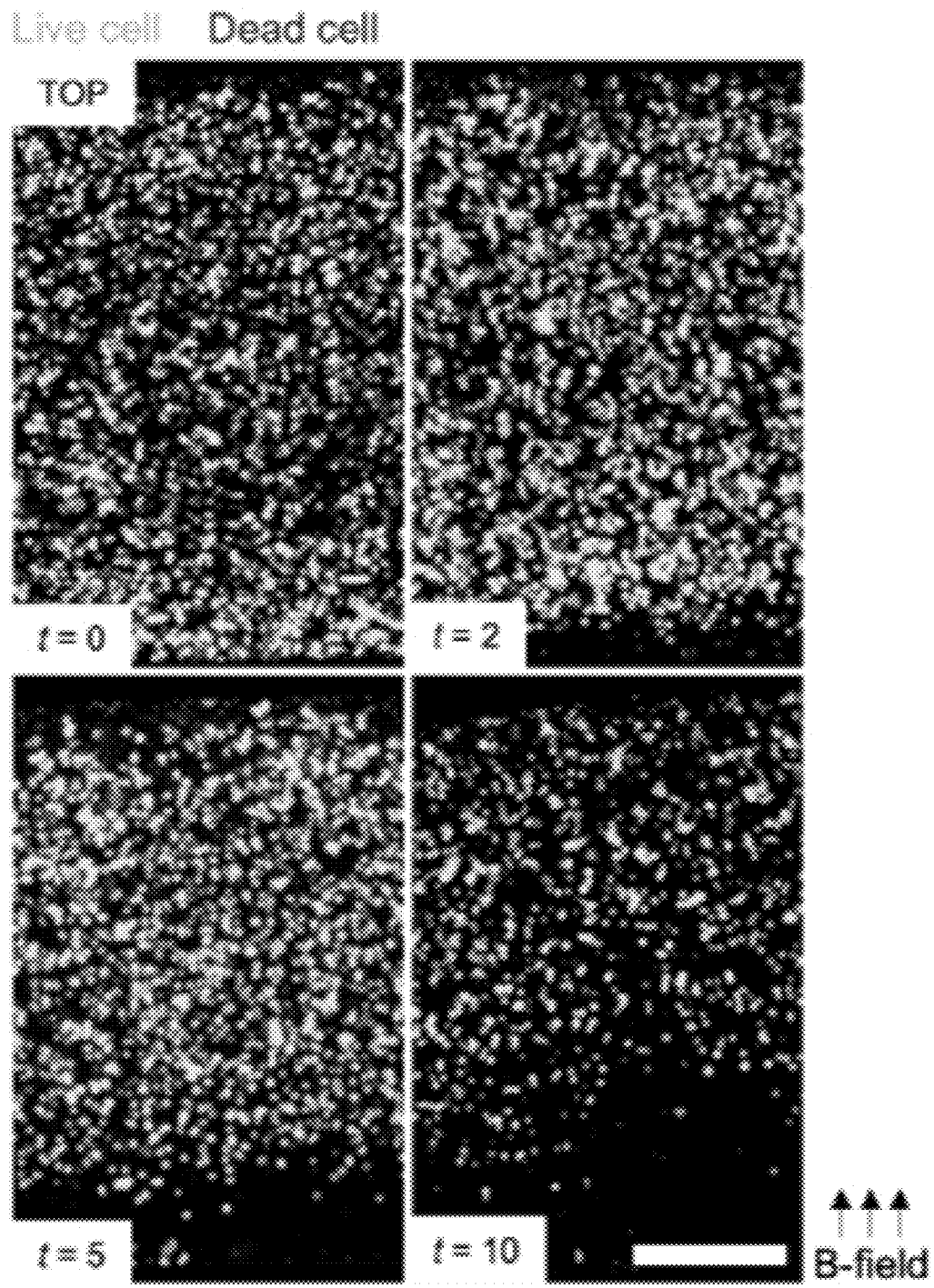
FIG. 7 shows images of cells exposed to a magnetic field over time.
Figure 8:
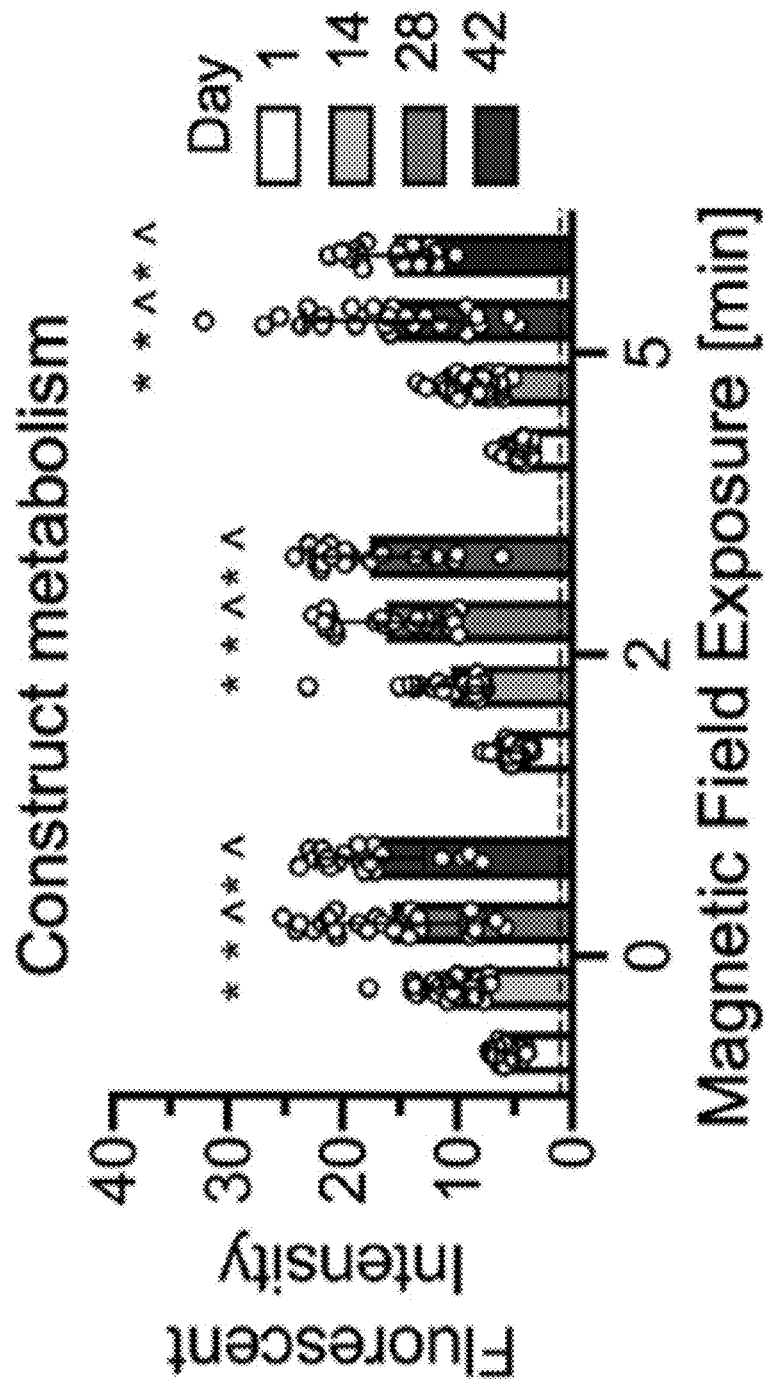
FIG. 8 shows a plot of cell metabolism in constructs over time.
Figure 9:
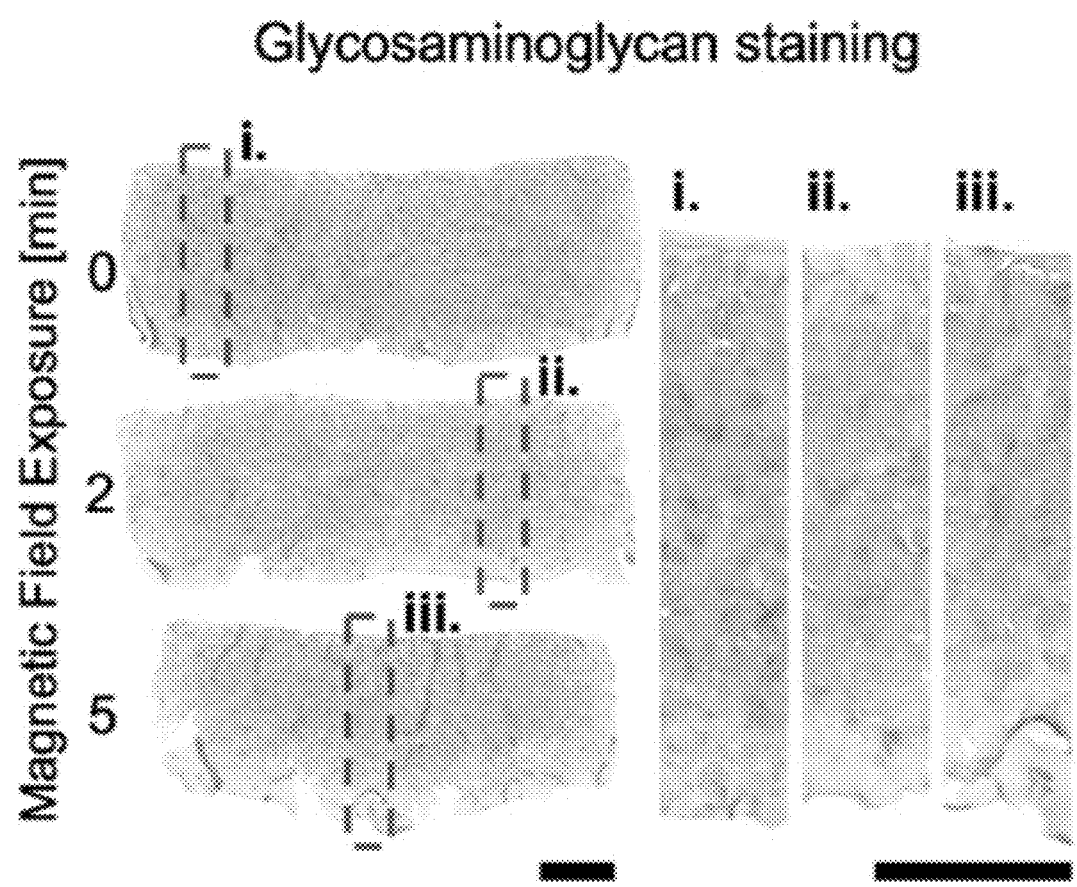
FIG. 9 shows matrix deposition in constructs. Constructs were cultured for 3 weeks and stained with Alcian blue (proteoglycans) and Picrosirius red (collagen). Scale=500 μm.
Figure 10:
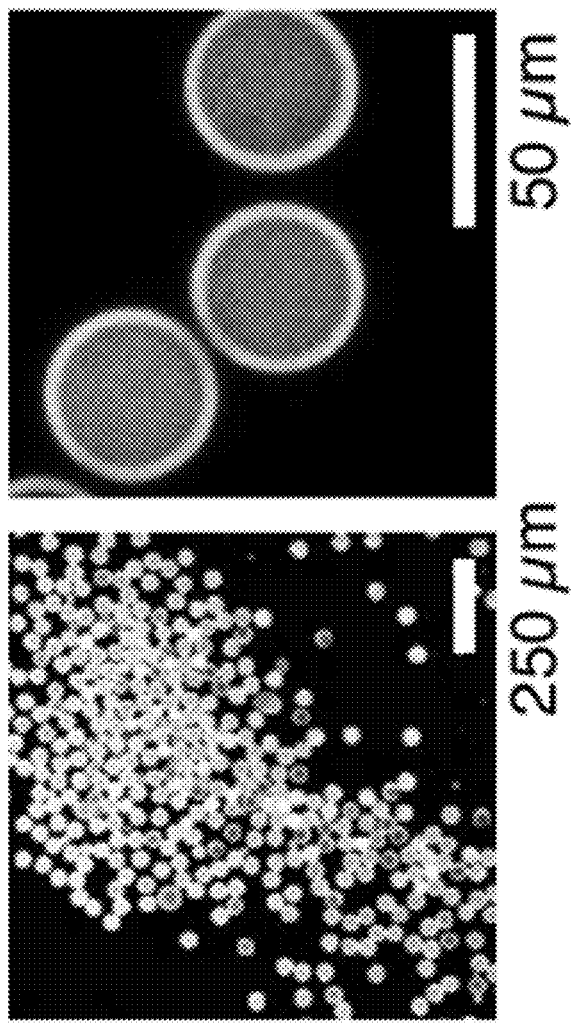
FIG. 10 shows images of intact paramagnetic microcapsules.

With reference to FIG. 6A, cell distribution after magnetic field exposure decreases in the bottom of constructs over time. FIG. 6B shows a plot of the % cells in a region of the construct over time. FIG. 7 shows a series of images demonstrating that cell viability is unaffected by magnetic field exposure over time. Calcein-AM is indicative of live cells, whereas Ethidium homodimer is indicative of dead cells. FIG. 8 shows that cell metabolism steadily increases over six weeks. An alamar blue assay was used to determine metabolic activity of the cells. FIG. 9 shows matrix deposition in constructs. Constructs were cultured for 3 weeks and stained with Alcian blue (proteoglycans) and Picrosirius red (collagen). Scale=500 µm. These results indicate that viable cells can be positioned within transiently paramagnetic hydrogels to recapitulate cartilaginous matrix gradients. The paramagnetic fluid, gadodiamide, is present for long enough to facilitate cell positioning, without requiring magnetic cell tags, which can inhibit chondrogenesis (Grogan+Tissue Eng 2012; Kostura+NMR Biomed 2004). This technology can be used to create other complex tissue interfaces in conjunction with any crosslinkable hydrogel and live cell population. With reference to FIG. 10, the technology can be used in conjunction with paramagnetic microcapsules capable of delivering a drug to target tissue or bone.

F. REFERENCES

Jin X, Zhao Y, Richardson A, Moore L, Williams P, Zborowski M, Chalmers J. "Differences in magnetically induced motion of diamagnetic, paramagnetic and superparamagnetic microparticles detected by cell tracking velocimetry." The Analyst. 2008; 133(12):1767-1775.

Li C, Armstrong J, Pence I, Worrapong K-A, Puetzer J, Carreira S, Moore A, Stevens M. "Glycosylated superparamagnetic nanoparticle gradients for osteochondral tissue engineering." Biomaterials. 2018; 176:24-33.

Grogan S, Pauli C, Chen P, Du J, Chung C, Kong S, Colwell C, Lotz M, Jin S, D'Lima D. "In Situ Tissue Engineering Using Magnetically Guided Three-Dimensional Cell Patterning." Tissue Engineering: Part C. 2012; 18(7): 496-506.

Tocchio A, Durmus N, Sridhar K, Vigneshwaran M, Coskun B, Assal B, Demirci U. "Magnetically Guided Self-Assembly and Coding of 3D Living Architectures." Advanced Materials. 2018; 30:170534.

Klein, T J et al., JOR, 40:182-190, 2007. [2] Zhu, D et al., Tissue Eng Part A, 24:1-10, 2018.

Kim, M et al., Acta Biomat, 58:1-11, 2017.

Ng, K W et al., Tissue Eng, 15(9): 2315-2324, 2009.

Anil-Inevi, M et al., Sci Rep, 8:1-10, 2018.

Shen, F et al., Analyt Chem, 84:3075-3081, 2012.

Durmus, N G et al., PNAS, 112:E3661-E3668, 2015.

Kostura, L et al., NMR Biomed, 17:513-517, 2004.

Burdick, J A et al., Biomacromol, 6:386-91, 2005.

It will be apparent to those skilled in the art that various modifications and variations can be made in the present disclosure without departing from the scope or spirit of the disclosure. Other embodiments will be apparent to those skilled in the art from consideration of the specification and practice of the disclosure. It is intended that the specification and examples be considered as exemplary only, with a true scope and spirit of the disclosure being indicated by the following claims.

What is claimed is:

1. A method of producing a continuous hydrogel material, the method comprising the steps of:
   (a) providing a viscous mixture comprising a hydrogel precursor, a paramagnetic or superparamagnetic salt, magnetic objects comprising a magnetic material and an active agent, crosslinking agent, and cells in a mold, wherein the cells are (i) not labeled with any magnetic label, (ii) do not have any magnetic particles tethered to or within the cells, and (iii) are diamagnetic;
   (b) creating a gradient of the cells in the viscous mixture through negative magnetophoresis by exposing the viscous mixture to a magnetic field, wherein exposing the viscous mixture to the magnetic field further creates a gradient of the magnetic objects in the viscous mixture that is opposite the gradient of the cells in the viscous mixture; and
   (c) crosslinking the hydrogel precursor, thereby producing the continuous hydrogel material having a gradient of the cells that is opposite the gradient of the magnetic objects.

2. The method of claim 1, wherein the viscous mixture has a viscosity of from about $10^{-2}$ to about 1 Pascal-second (Pa·s) at ambient temperature.

3. The method of claim 1, wherein exposing the viscous mixture to the magnetic field comprises positioning a magnet close to the mold.

4. The method of claim 1, wherein exposing the viscous mixture to the magnetic field comprises exposing the viscous mixture to from about 1,000 Oersted (Oe) to about 5,000 Oersted (Oe).

5. The method of claim 1, wherein crosslinking the hydrogel precursor comprises ultraviolet or visible light exposure, heating, or altering the pH of the viscous mixture.

6. The method of claim 1, wherein the active agent is a bone promoting agent.

7. The method of claim 1, wherein the continuous hydrogel material is formed from poly(ethylene oxide), poly(vinyl alcohol), poly(acrylic acid), poly(propylene fumarate-co-ethylene glycol), poly(ethylene glycol), a polypeptide, agarose, alginate, chitosan, collagen, fibrin, gelatin, hyaluronic acid, or a combination thereof.

8. The method of claim 1, wherein the paramagnetic or superparamagnetic salt is paramagnetic and comprises a salt of gadolinium, manganese, iron, chromium, cobalt, nickel, or neodymium.

9. The method of claim 1, further comprising (d) washing at least a portion of the paramagnetic or superparamagnetic salt out of the continuous hydrogel material.

10. The method of claim 1, wherein the magnetic objects comprise a magnetic material in a superparamagnetic, paramagnetic, ferromagnetic, or ferrimagnetic state.

11. The method of claim 1, wherein the magnetic objects comprise a microcapsule.

12. The method of claim 6, wherein the bone promoting agent comprises a calcium source, a phosphate source, bone morphogenetic factor, an anti-resorptive agent, an osteogenic factor, a cartilage-derived morphogenetic protein, a growth hormone, an estrogen, a biphosphonate, a statin, a differentiation factor, or a combination thereof.

13. The method of claim 1, wherein the cells are naturally diamagnetic.

14. The method of claim 1, wherein the gradient of the cells is linear throughout the viscous mixture and the continuous hydrogel material.

15. The method of claim 1, wherein the gradient of the cells is arranged along a longitudinal axis of the viscous mixture and the continuous hydrogel material.

16. The method of claim 1, wherein the gradient of the cells is arranged along a transverse axis to a longitudinal axis of the viscous mixture and the continuous hydrogel material.

17. The method of claim 1, wherein the gradient of the cells is such that a portion of the viscous mixture has at least twice the concentration of cells as compared to another portion of the viscous mixture.

18. The method of claim 1, wherein the gradient of the cells is such that a portion of the viscous mixture has at least five times the concentration of cells as compared to another portion of the viscous mixture.

19. The method of claim 1, wherein the gradient of the magnetic objects is such that a portion of the continuous hydrogel material has at least twice the concentration of objects as compared to another portion of the continuous hydrogel material.

20. The method of claim 9, comprising washing the paramagnetic or superparamagnetic salt out of the continuous hydrogel material.

* * * * *